(12) United States Patent
Herling et al.

(10) Patent No.: US 7,435,760 B2
(45) Date of Patent: Oct. 14, 2008

(54) METHOD OF GENERATING HYDROCARBON REAGENTS FROM DIESEL, NATURAL GAS AND OTHER LOGISTICAL FUELS

(75) Inventors: Darrell R Herling, Richland, WA (US); Chris L. Aardahl, Richland, WA (US); Robert T. Rozmiarek, Middleton, WI (US); Kenneth G. Rappe, Richland, WA (US); Yong Wang, Richland, WA (US); Jamelyn D. Holladay, Kennewick, WA (US)

(73) Assignee: Battelle Memorial Institute, Richland, WA (US)

( * ) Notice: Subject to any disclaimer, the term of this patent is extended or adjusted under 35 U.S.C. 154(b) by 475 days.

(21) Appl. No.: 11/128,488

(22) Filed: May 12, 2005

(65) Prior Publication Data

US 2005/0267224 A1    Dec. 1, 2005

Related U.S. Application Data

(60) Provisional application No. 60/571,457, filed on May 14, 2004.

(51) Int. Cl.
*C07C 27/00* (2006.01)

(52) U.S. Cl. .................. 518/700; 518/702; 518/703; 518/704

(58) Field of Classification Search .......... 518/700–704
See application file for complete search history.

(56) References Cited

U.S. PATENT DOCUMENTS

| | | | |
|---|---|---|---|
| 3,851,470 A | 12/1974 | Kaufmann, Jr. | |
| 3,862,899 A * | 1/1975 | Murphy et al. ................. | 208/93 |
| 5,324,335 A | 6/1994 | Benham et al. | |
| 5,412,946 A | 5/1995 | Oshima et al. | |
| 5,763,716 A | 6/1998 | Benham et al. | |
| 5,856,585 A * | 1/1999 | Sanfilippo et al. ........... | 568/470 |
| 6,086,751 A | 7/2000 | Bienstock et al. | |
| 6,156,084 A | 12/2000 | Bonville, Jr. et al. | |
| 6,698,191 B2 | 3/2004 | Xu et al. | |
| 2004/0267076 A1 | 12/2004 | Josephus | |

FOREIGN PATENT DOCUMENTS

| | | |
|---|---|---|
| WO | WO 2004/011574 A | 2/2004 |
| WO | WO 2004046514 A1 | 6/2004 |

OTHER PUBLICATIONS

PCT Invitation to Pay Additional Fees dated Aug. 14, 2006.

* cited by examiner

*Primary Examiner*—Jafar Parsa
(74) *Attorney, Agent, or Firm*—Derek H. Maughan (57) ABSTRACT

The present invention provides a process for producing reagents for a chemical reaction by introducing a fuel containing hydrocarbons into a flash distillation process wherein the fuel is separated into a first component having a lower average molecular weight and a second component having a higher average molecular weight. The first component is then reformed to produce synthesis gas wherein the synthesis gas is reacted catalytically to produce the desire reagent.

11 Claims, 5 Drawing Sheets

METHOD OF GENERATING HYDROCARBON REAGENTS FROM DIESEL, NATURAL GAS AND OTHER LOGISTICAL FUELS

RELATED APPLICATION

This application claims the benefit of provisional application 60/571,457 filed 5/14/2004.

The invention was made with Government support under Contract DE-AC0576RLO 1830, awarded by the U.S. Department of Energy. The Government has certain rights in the invention.

TECHNICAL FIELD

This invention relates generally to a process for producing reagents to minimize NOx emissions derived from internal and external combustion engines. More particularly, the invention relates to a process for producing reagents using a three step process to transform fuel hydrocarbons into reagent species in a manner that allows for high activity and control over the selectivity of the resultant reagents.

BACKGROUND OF THE INVENTION

More stringent environmental regulations require novel approaches to minimize NOx emissions from major sources, such as on-road and off-road vehicles. Current logistic fuels, such as diesel, kerosene, JP-8, gasoline, and natural gas are the preferred choice as reductants for NOx reduction aftertreatment systems, such as hydrocarbon selective catalytic reduction (HC-SCR) and lean NOx traps (LNT). This is primarily due to the fact that such fuels are already carried on-board a vehicle as the combustion fuel for the engine and, therefore no special secondary treatment is required. However, the direct use of these fuels as reducing agents in catalytic aftertreatment systems is known. Hydrocarbon species which make up the fuel are not the actual reductant used in NOx reduction chemistry. Instead, most catalyst formulations contain one or more "promoters", which are typically made up from precious metals or base metal oxides, whose function is to "convert" fuel hydrocarbons into partially oxidized species like alcohols, aldehydes or ketones. It is these oxygenates that are active in the chemical reduction of NOx on the surface of most lean-NOx catalysts.

Currently, some of the most active reductants for HC-SCR are aldehydes and alcohols such as methanol, ethanol, acetaldehyde, and formaldehyde. On-board production of these reductants would allow for better performance of the catalyst system to meet the more stringent environmental regulations for NOx emissions. The enhanced performance of aldehydes and alcohols over traditional hydrocarbons (propylene) is based on the broadening of the active temperature window, higher selectivity, and higher overall activity for reduction of NOx.

Accordingly, the ability to transform fuel hydrocarbons into oxygenated species in a manner that allows for high activity and control over the selectivity would be a breakthrough in the aftertreatment industry. The invention described herein provides for a method to produce specific oxygenates from diesel, natural gas, JP-8, and other hydrocarbon fuels.

SUMMARY OF THE INVENTION

One embodiment of this invention provides a process for producing reagents for a chemical reaction by introducing a fuel containing hydrocarbons into a flash distillation process, wherein the fuel is separated into a first component having a lower average molecular weight and a second component having a higher average molecular weight. In yet a further embodiment, the present invention provides a process to reform the first component to produce a mixture of predominately synthesis gas. In yet a further embodiment, the present invention provides a process to react catalytically the synthesis gas to produce desired reagent. The desired reagents may be selected from a group consisting of ethers, alcohols, and combinations thereof. Preferably, but not to be limiting, the ether may be dimethyl ether, and the alcohol may be methanol. The reagent may further be a mixture of dimethyl ether to methanol in approximately a 4:1-8:1 ratio on a molar basis. It is also contemplated that the reagents produced by this invention may be olefinic products, keytone products, aldehyde products, and combinations thereof, depending on the catalyst used in the chemical synthesis.

In another embodiment, the present invention provides a process as described herein, wherein the sulfur is reduced to at least 20 ppb before catalytically reacting the synthesis gas to desired reagent.

In still another embodiment, the present invention provides a process to create a fuel supplement feedstock for a power source. The power source may be a fuel cell, for example, but not to be limiting, a solid oxide fuel cell, molten carbonate fuel cell, a phosphoric acid fuel cell, a direct methanol fuel cell that may handle dimethyl ether, proton exchange membrane fuel cell, or an auxiliary power unit fuel cell. Another power source may be internal or external combustion engine, such as a rotary engine or stirling engine, or a heat pump wherein the DME is used to drive the thermal compression cycle.

In a further embodiment, the present invention provides a process for producing a feedstock as described herein for use in a lean-NOx exhaust system.

In a further embodiment, the present invention provides a reforming step as selected from a group consisting of partial oxidation, catalytic partial oxidation, autothermal, steam reforming, plasma reforming, super critical reforming, cracking, dry reforming and combinations thereof. Also, the invention may utilize catalysts selected from the group of precious metals, for example, but not to be limiting, ruthenium, rhenium rhodium, palladium, silver, osmium, iridium, platinum, and gold to achieve a desired reagent during the reforming step.

In another embodiment, the present invention provides a process described herein used for producing reagents for use in lean-NOx exhaust systems. In this embodiment, fuel containing hydrocarbons is introduced into a reforming unit operably connected offline from an engine exhaust system to produce a synthesis gas. The synthesis gas is then reacted catalytically to produce desired reagents. In this embodiment, the reagents may be selected from the group consisting of ethers, alcohols, and combinations thereof. More preferably, but not to be limiting, the ether may be dimethyl ether, and the alcohol may be methanol. It may also be desired to have the reagents comprise a mixture of dimethyl ether to methanol in approximately a 4:1-8:1 ratio on a molar basis. The reforming unit may incorporate one or more of the operations from the group consisting of partial oxidation, catalytic partial oxidation, autothermal, steam reforming, plasma reforming, super critical reforming, cracking, dry reforming and combinations thereof. As used herein and throughout this patent, reforming means producing synthesis gas from hydrocarbons.

In a further embodiment of this invention, the sulfur is reduced to at least 20 ppb before reacting catalytically the synthesis gas to produce desired reagents.

In a still further embodiment of this invention, the reagents are selected from a group consisting of olefinic products, keytone products, aldehyde products, and combinations thereof.

In another embodiment of this invention, the process described herein is used in a hydrocarbon selective catalyst reduction system.

In a still further embodiment of this invention, the process provides a method for reducing soot and NOx in the combustion process. In this embodiment, a fuel containing hydrocarbon is introduced into a first step comprising a flash distillation process. It is then separated into a first component having a lower average molecular weight and a second component having a higher average molecular weight. The first component is then reformed to produce a mixture consisting predominantly of synthesis gas. The synthesis gas is then reacted catalytically to produce a reagent. The reagent is then reintroduced into the combustion process. The reagent may be selected from the group consisting of ethers, alcohols, and combinations thereof. Preferably, but not to be limiting, ether is dimethyl ether, and the alcohol is methanol. It may also be preferred to remove any gas that may be present in the effluent during the catalytic reaction.

In another embodiment, the invention described herein provides a process for reducing sulfur contaminates and other additives from a liquid hydrocarbon fuel source. In this embodiment, the flash distillation process is used to separate the fuel into a first component having a lower average molecular weight and a second component having a higher molecular weight. Preferably, but not to be limiting, the additive, sulfur, and detergent compounds are thus removed from the first component because they have a partial pressure less than first component.

BRIEF DESCRIPTION OF THE DRAWINGS

The following detailed description of the embodiments of the invention will be more readily understood when taken in conjunction with the following drawing, wherein.

DETAILED DESCRIPTION OF THE PREFERRED EMBODIMENTS

Flash Distillation

A series of experiments were conducted to demonstrate various embodiments and advantages of the present invention. In the first of these experiments, a fuel containing hydrocarbons was introduced into a flash vessel as described herein. The flash distillation process separates the fuel into two streams, a vapor and a liquid. The vapor stream will contain predominantly lighter hydrocarbons, while the liquid product will maintain the heavier fraction including many of the sulfur laden molecules. The fuel is heated to a temperature in the range of about 100-400° C. under a pressure of about 5-80 atmospheres and "flashed" across a valve to a lower pressure between about 0.5 and 30 atmospheres (absolute). The vapor and liquids are thus separated in a flash vessel. The recovered lighter component of the hydrocarbon stream, by example and not to be limiting, has a molecular structure averaging between about five carbon atoms per molecule (C5) and about eight carbon atoms per molecule (C8). The recovered heavier component of the hydrocarbon stream, by example and not to be limiting, has a molecular structure averaging between about ten carbon atoms per molecule (C10) and about eighteen carbon atoms per molecule (C18). The lighter component also has a lower amount of sulfur than the heavier component.

Figure 1:
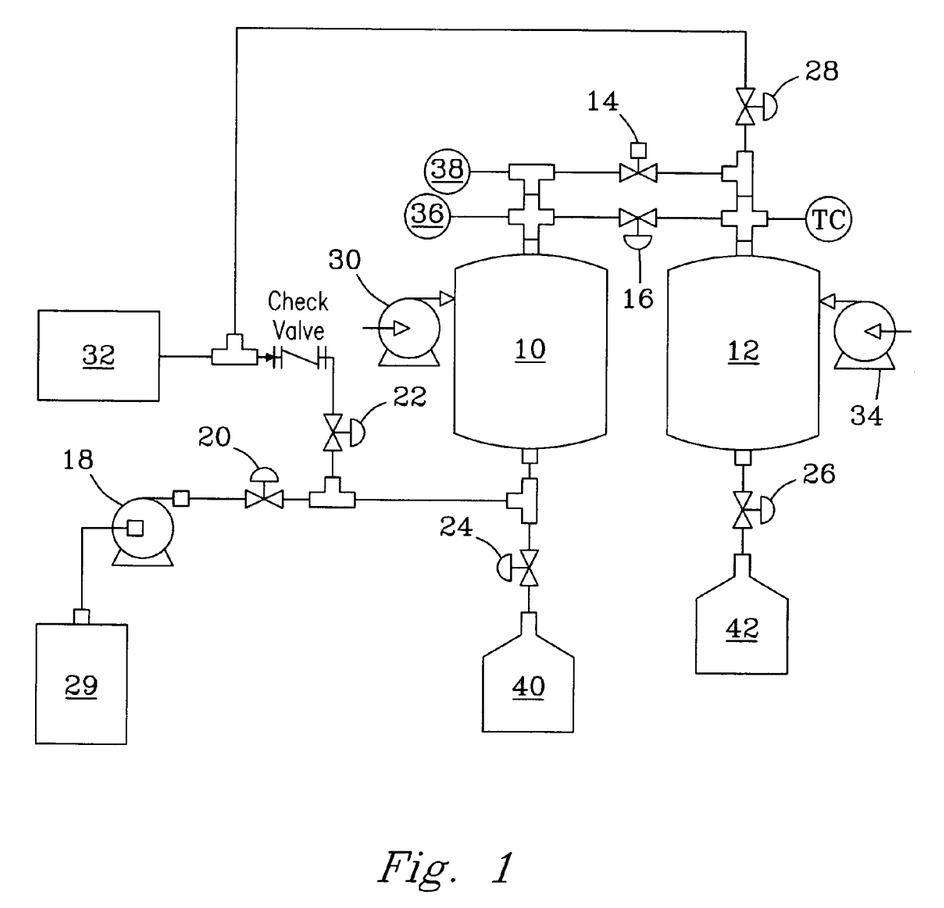
FIG. 1 is a schematic drawing of batch flash distillation process.

Referring now to the drawings, FIG. 1 is a schematic view of the flash distillation process used in proof-of-principle experiments designed to demonstrate the advantages of certain embodiments of the present invention. The batch system is preferably made up of two high pressure vessels; the 75 ml flash vessel 10 and the 75 ml condenser vessel 12, a solenoid valve 14, a back pressure regulator 16, and a microgear pump (Micopump-MZR-7205) 18. Valves 20, 22, 24, 26, 28 are utilized to open and close the typical ⅛ in. stainless steel line while operating the system. A Julabo oil pump 30, capable of pumping 14-18 lpm, may be used to heat the flash vessel 10 to approximately 320° C. In this embodiment, a fuel tank 29 containing diesel fuel of DBT, 4 methyl DBT and 4,6 methyl DBT with a concentration between about 50 and about 3073 ppmw of sulfur was connected to a ⅛' stainless steel tube to allow the fuel to travel throughout the system. The fuel is pumped into the flash vessel 10 by the microgear pump 18. The fuel was pressurized using a mass flow controller 32 (Brooks 5850 E), which pumped nitrogen gas throughout the system. The condenser vessel 12 was also jacketed, and a typical liquid pump 34 capable of pumping 14-18 lpm may be used to pump cooling water through the jacket to cool it. Cooling water was maintained between 13-15° C. The vessels and any stainless steel tubing which was to be contacted by the diesel were treated with Sulfinert™ (Restek Corp.). The Sulfinert™ coating passivated the stainless steel so that it would not adsorb sulfur while still enabling the tubing to be bent and shaped. This coating is stable to 400° C. in inert atmospheres.

After purging the system with nitrogen for several minutes, valve 24 was shut and 20 ml of fuel was fed to the flash vessel. The nitrogen purge was left on at 25 sccm while the fuel was pumped in. Valve 20 was then closed and the flash vessel was pressurized with the nitrogen to the desired pressure identified in Table 1. Preferably, but not meant to be limiting, the flash pressure at this point is lower than the final pressure desired. While the flash vessel 10 is being pressurized, it was also heated. A pressure transducer 36 was used to measure the pressure of the flash vessel 10. The condenser vessel 12 was pressurized by closing valve 26. Once the desired temperature was reached, additional nitrogen could be used to finish pressurizing the system as needed. The solenoid valve 14 is then opened for approximately 3 seconds for the flash to occur. A thermocouple 38 measured the light component being flashed off. The system is then cooled and the separated materials collected. The condenser vessel 12 temperature was maintained at approximately 13° C. The heavier component was captured in vessel 40 to be reintroduced back into the fuel 29. The lighter component, which flashed off the fuel was captured in vessel 42 and then sent to a reformer to produce synthesis gas. Some typical results and conditions are shown in Table 1.

TABLE 1

| Sample | Initial sulfur ppm | P flash at T (psi) | T flash (C) | P condenser initial (psi) | % Flashed (%) | Final Sulfur ppm | % Reduced Sulfur |
|---|---|---|---|---|---|---|---|
| 1 | 3073 | 211 | 297 | 6.6 | 5.3% | 868 | 71% |
| 2 | 3073 | 300 | 320 | 100 | 7% | 1040 | 66% |
| 3 | 3073 | 455 | 326 | 200 | 2% | 1122 | 63.5% |
| 4 | 1002.3 | 209 | 302 | 8.6 | 12.5% | 419.3 | 58% |
| 5 | 1002.3 | 303 | 314 | 102 | 4.9% | 403.5 | 59% |
| 6 | 1002.3 | 430 | 324 | 201 | 3.7% | 385 | 61% |
| 7 | 529.7 | 200.1 | 283 | 7.8 | 2.7% | 189.4 | 64% |
| 8 | 529.7 | 309.4 | 321 | 104.1 | 4.9% | 198 | 63% |
| 9 | 529.7 | 447 | 326 | 204 | 3.7% | 191 | 64% |
| 10 | 50.1 | 210 | 302 | 6.7 | 17.5% | 20.6 | 59% |
| 11 | 50.1 | 301.5 | 325 | 103 | 7.3% | 21 | 58% |
| 12 | 50.1 | 429.5 | 324 | 201 | 2.4% | 26 | 48% |

The present invention typically utilized a condenser pressure of imately 5-200 psi, depending on the operating parameters. Accordingly, lash vessel is heated to approximately 300-320° C., there needs to be a 200-250 psi pressure difference to recover approximately 5% of the fuel.

Reforming Process

In the first of these experiments, a partial oxidation process was used as the reforming process. The partial oxidation (POx) reaction is an exothermic process (methane: ΔH=−36 kJ/mol; decane: ΔH=−856 kJ/mol) and requires no additional energy for operation.

$$C_nH_m+(n/2)O_2 \rightarrow nCO+(m/2)H_2$$

The POx process in the present invention typically produces a lower $H_2$:CO ratio than is formed by steam reforming. It is not necessarily an equilibrium controlled process, and thus product distribution ($H_2$:CO ratio) is under limited control beyond controlling the proper C/O ratio, the reforming catalyst formulation, and the catalyst contact time (space velocity [SV]). POx operates at higher temperatures (in excess of 600° C.) in comparison to steam reforming, and thus demonstrates increased sulfur tolerance. Additionally, one skilled in the art would recognize that the POx process has a greater resistance to carbon depositing and fouling, provided oxygen to carbon levels are sufficient.

Figure 2:
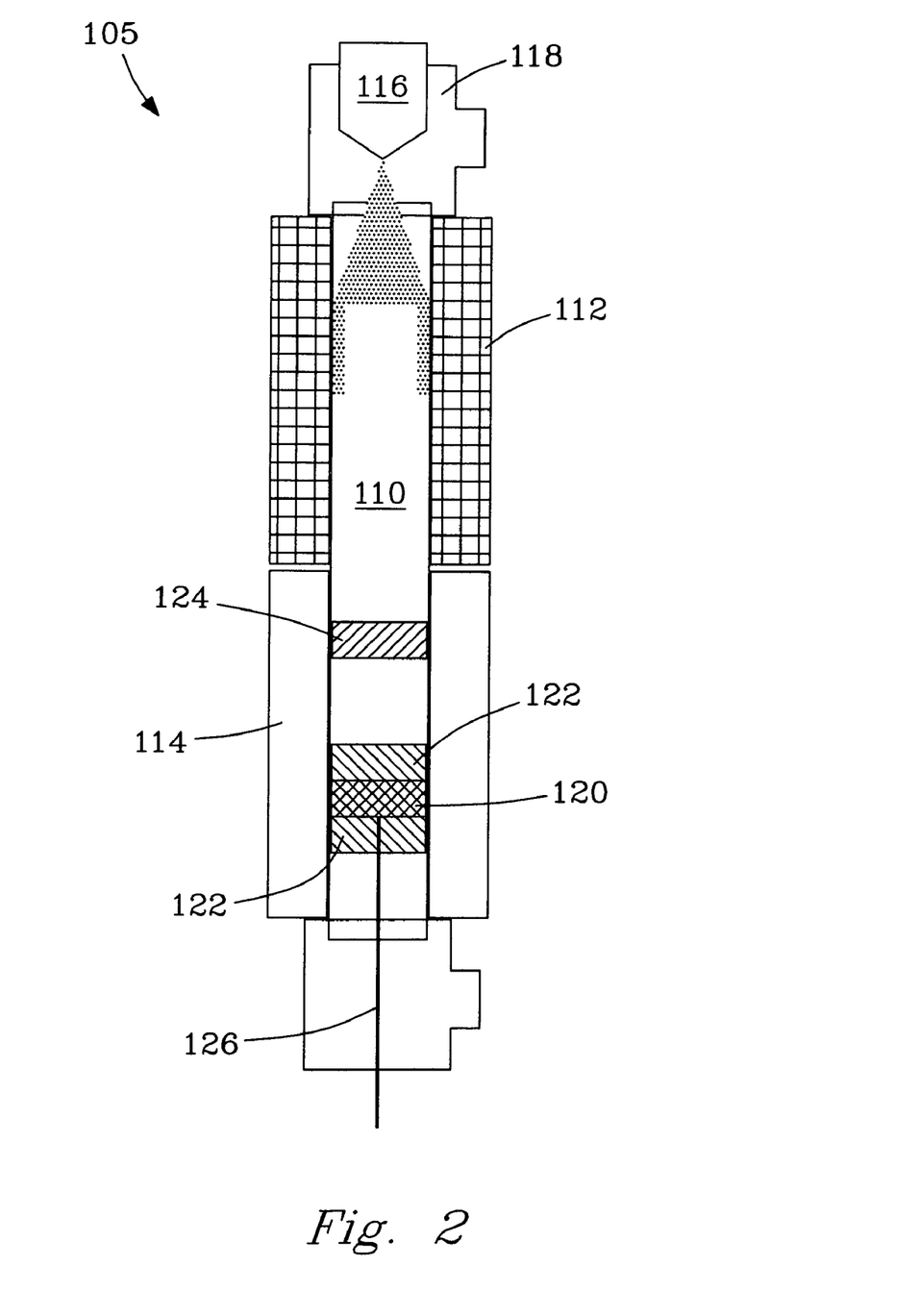
FIG. 2 is a schematic drawing of the millisecond contact time Pox reactor.

The present invention employed a millisecond contact time reactor as a reformer to convert either diesel or natural gas to largely synthesis gas components in addition to minimal amounts of carbon dioxide. FIG. 2 shows a schematic of the millisecond contact time reformer employed in the initial investigations of the partial oxidation process.

In one typical embodiment. the POx reactor 105 facilitates the vaporization of fuel in air and then passes this air-fuel mixture over a Rh or Rh—Pt supported on γ-alumina or a Rh-Pt gauze (Johnson Mathey, Engelhard) which facilitates the fuel POx process. The reactor 105 consists of a 2 ft (610 mm) long, 25 mm OD quartz tube 110 surrounded by a cylindrical furnace 112 on the upper half of the tube and insulation 114 on the bottom half. Fuel vaporization is assisted by a fuel injector 116 that forms a spray to create a film of fuel on the inside of the quartz tube at the top of the reactor. The fuel injector is fasted inside a stainless steel "T" fitting 118 (Swaglock Company). The fitting 118 coupled together the top of the reactor tube with the fuel injector. The fitting was sealed to the reactor tube using a typical Teflon ferrule. Vaporization of fuel is facilitated by the cylindrical furnace 112, and the fuel is sprayed forming a film on the inside of the reactor tube. The fuel vaporizes off the inside to the tube 110 and forms a boundary layer void of oxygen, in addition to the liquid film produced by the fuel injector 116 to avoid autothermal ignition of the fuel. The Rh-catalyst 120 consists of a γ-alumina layer deposited onto an 80-ppi reticulated ceramic support 122 (Hi-Tech Ceramics), with Rh deposited onto the γ-alumina layer via Rh-nitrate solution. Blank reticulated ceramic supports 122 are placed directly upstream and downstream so as to be in thermal contact of the catalyst for heat shielding, and another blank support 124 is placed in upstream to sufficiently promote mixing and facilitate plug flow. The catalyst 122 and blank supports 124 are wrapped in fiberfrax paper to hold each in place and avoid bypassing of flow around the supports. A mineral insulated thermocouple 126 (Watlow, type K) monitors the temperature on the back face of the catalyst 120 which is sealed with a graphite ferrule. A second stainless steel "T" fitting was sealed to the bottom of the reactor tube to divert the product stream for characterization. The "T" fitting was sealed using a typical graphite ferrule. The characterization of the POx product stream was performed with a typical gas chromatograph (GC) commercially available from Agilent Technologies equipped with a thermal conductivity detector (TCD) and a mass selective detector (MSD)(model number 5973).

In another typical embodiment, a steam reforming process was utilized as the partial oxidation step. Steam methane reforming (SMR) is a widely used catalytic commercial process in the chemical industry today. The SMR reaction consists of two main reactions, the SMR reaction [1] and the water-gas shift reaction [2].

$$C_nH_m+(n)H_2O \rightarrow (n)CO+(m/2+n)H_2 \quad [1]$$

$$CO+H_2O \leftrightarrow CO_2+H_2 \quad [2]$$

$$\text{Net: } C_nH_m+(2n)H_2O=(n)CO_2+(m/2+2n)H_2 \quad [3]$$

The steam reforming reaction is highly endothermic (methane: ΔH=+206 kJ/mol; decane: ΔH=+1563 kJ/mol), while the water-gas shift reaction is slightly exothermic (ΔH=−41 kJ/mol). The combined process (3) is highly endothermic, requiring a high temperature for favorable equilibrium conversion. As contemplated by the present invention, the synthesis gas may further be processed by any of the methods including, but not limited to, methanol synthesis, ammonia synthesis, Fischer-Tropsch synthesis, and the manufacture of hydrogen ($H_2$): and the products then used either as fuels or as reagents in engines and/or fuel cells.

Chemical Synthesis

Synthesis gas typically comprises a mixture of CO and hydrogen and can be converted to a variety of fuels and chemicals using known chemistries. Methanol synthesis is typically conducted over Cu based catalysts at temperatures from 200 to 400° C. and pressures from approximately 20-100 atm. The catalysts typically contain 55 wt % CuO, 25 wt % ZnO, and 8 wt % alumina and are typically made by co-precipitation of Cu, Xn, and Al. High pressure and low temperature favor the equilibrium CO conversion to methanol. To overcome the equilibrium limitation, acid type catalysts such as acidic alumina or zeolites were added in the synthesis step to shift methanol to DME. DME can also be synthesized in a separate step from methanol by general dehydration of methanol to produce DME on acidic catalyst, such as acidic alumina and zeolites. This process is typically conducted at temperatures from 200-350° C. Synthesis gas can also be converted to high alcohols, such as ethanol, propanol, butanol, pentanol using alkali doped Cu catalyst, MoS2 catalyst, or Rh based catalyst for high alcohol synthesis. High alcohol synthesis is typically conducted at 200-400° C. and pressures approximately from 20-100 atm. Alternatively, synthesis gas can be converted to olefins on Co or Fe-based catalysts (SASOL) using Fichser-Tropsch synthesis at temperatures from 200 to 400° C. and typical pressures of approximately 20-100 atm. High alcohols can also be dehydrated over acidic catalysts like alumina or zeolite (UOP, Grace Division or Amberlyst) to form ethers or olefins at temperatures from 100-400° C. Alcohols can also be further converted to aldehydes over early transition metal oxides or commercially available Ag based catalysts (ABB Lummus, Globall, Haldor Topsoe) in the presence of oxygen in the temperatures from 200 to 750° C. For example, and not to be limiting, methanol can be selectively oxidized to form formaldehyde using oxygen over Fe—Mo catalysts at temperatures from approximately 300-500° C., and over the Ag catalysts at temperatures from 650 to 800° C.

A mixture of methanol synthesis and dehydration catalysts was used to test direct synthesis of synthesis gas to produce DME. The experiments were carried out in a microchannel reactor (316 stainless steel), with the dimensions of 5.08 cm×0.94 cm×0.15 cm. The methanol synthesis catalyst was CuZnAl, based and purchased from Kataco Corporation (F51-8PPT); and the dehydration catalysts can be either ZSM-5 zeolite with a Si/Al ratio of 30 (Zeolyst International) or acidic $Al_2O_3$ (Engelhard Corporation) with ZSM-5. Both the methanol synthesis catalyst and the dehydration catalyst were crushed and sieved into 70-100 mesh. The catalyst mixture was prepared by mechanically mixing the two types of catalysts in a transparent vial at a desired ratio and charged in the microchannel reactor. Typically, 0.18 or 0.36 grams catalyst was used. The volume of the catalyst $+Al_2O_3$ was approximately 0.366 cc and 0.731 cc, respectively.

In one embodiment, the experimental conditions comprised temperatures from 220-320° C. and pressure from 2-5 MPa. The catalyst mixture (mixture of methanol synthesis and ZSM-5 or acidic alumina) was reduced with 10% hydrogen in helium in the 220-350° C. temperature range at atmospheric pressure. A mixture of $N_2/H_2$ was fed during startup to establish steady-state flow and to heat the reactor to the desired temperature. When the catalyst bed temperature reached the target, premixed synthesis gas at the desired ratio was fed into the reactor. After reduction was complete, the desired temperature was achieved by ramping it at 1° C./min. The pressure was also increased to the desired operating condition (between 100-300 psig). The feed was initiated at this time.

The ratio of typical feed composition was $CO:H_2:CO_2$: Ar=30:62:4:4. The presence of Ar served as the internal standard for conversion and selectivity calculation purposes. Total feed flow rate was set to achieve the desired gas hourly space velocity (GHSV). The reaction products were analyzed by on-line gas chromatography (HP 5890 GC) equipped with both TCD and FID detectors. GC column used is GS-Q 30 m manufactured by JW Scientific. Temperature program of 5° C./min to 300° C. was chosen for the analysis. Liquid products were collected in a cold trap at −3° C. and were also analyzed by GC-mass spectrometry. Carbon monoxide conversion and product selectivity were calculated, based on feed and product flow rates and carbon balance.

Primary or secondary alcohols can be dehydrogenated to form aldehydes or ketones on copper chromite or ZnO—Cr2O3, or alumina supported Pt or Raney Ni catalysts (Engelhard, Celanese, Johnson Mathey, or Sud-Chemie) from about 200 to 400° C.

Figure 3:
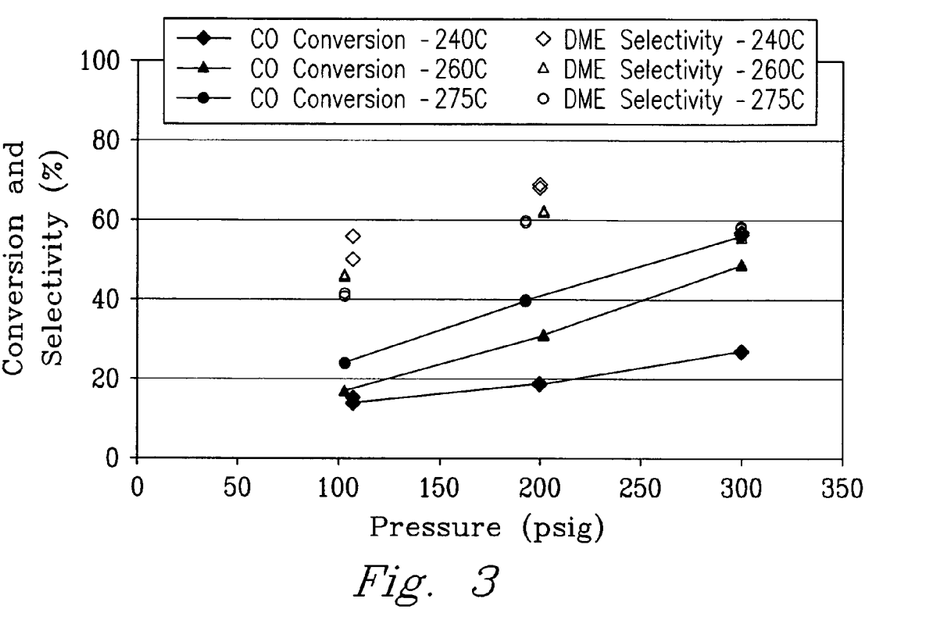
FIG. 3 illustrates the pressure and temperature effects on conversion and selectivity.
Figure 4:
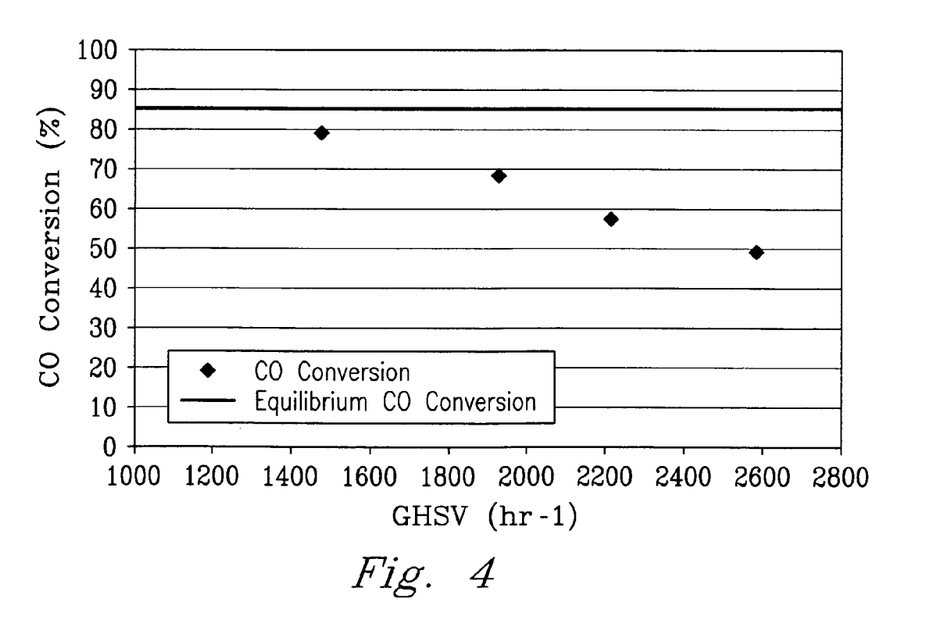
FIG. 4 illustrates Effect of GHSV on CO Conversion.
Figure 5:
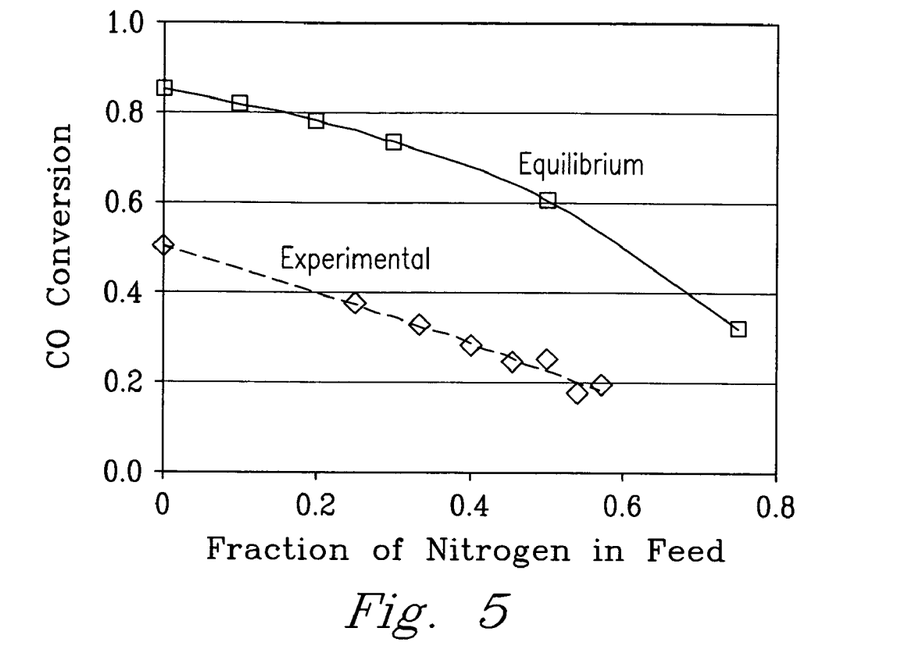
FIG. 5 illustrates the Nitrogen ($N_2$) Dilution Effects on DME Synthesis.
Figure 6:
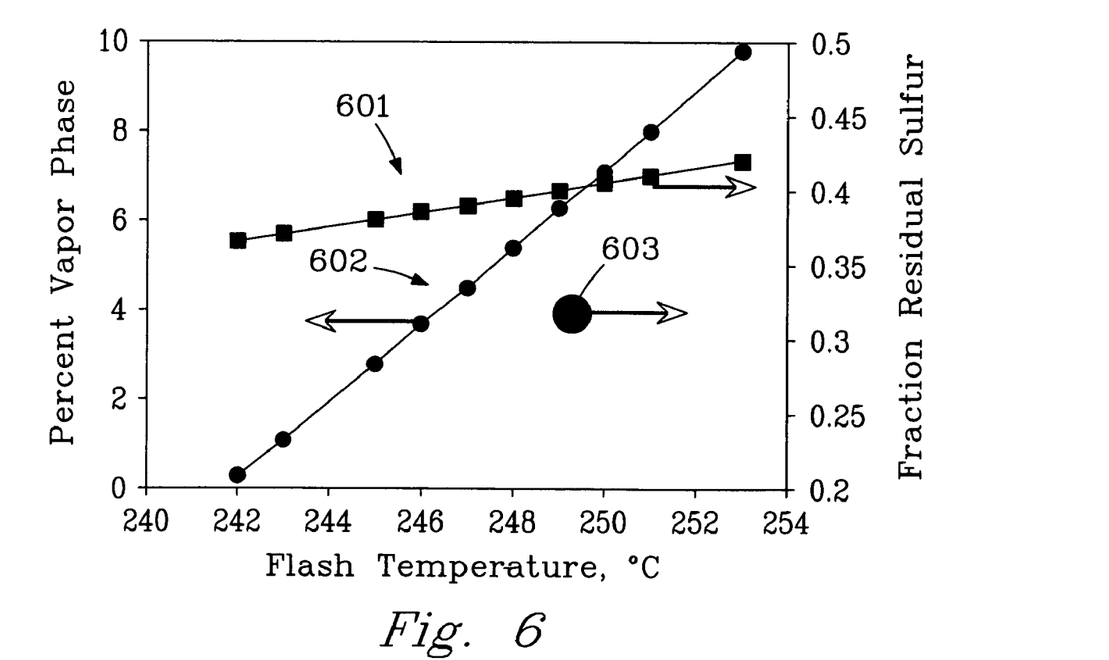
FIG. 6 illustrates the flash distillation with 1000 ppm Dibenzothiophene inlet.

Typical compositions of the effluents coming out of the chemical synthesis process were 60% DME, 30% $CO_2$, and 10% methanol. FIG. 3 shows that the CO conversion increased with increasing temperature and pressure. FIG. 4 shows the CO increased with a reduction in the Gas Hourly Space Velocity (GHSV). As the GHSV is decreased (residence time is increased) CO conversion approaches equilibrium and will reach equilibrium at about 1400 1/hr at a pressure of 200 psig and a temperature of 260° C. Likewise, as the residence time decreases, so does the CO conversion. Since the feed gas is going to be the product from a POx, it will be diluted with nitrogen. FIG. 5 shows activity of CO conversion during the chemical synthesis process at various dilution of N2. Equilibrium shows that with an increase in dilution, there is a decrease in CO conversion. The present invention experimental data shows that it follows the equilibrium trend. FIG. 6 illustrates the flash distillation results for 1000 ppm sulfur in the form of DBT, 4 methyl DBT and 4,6 methyl DBT. 601 represents the theoretical fraction of residual sulfur in the lower molecular weight component. 602 represents the theoretical fraction of the lower molecular weight component of the feedstock fuel. 603 represents the experimental results from the present invention. FIG. 6 further illustrates the present invention achieved 0.32 fraction of residual sulfur, indicating that the amount of sulfur in the fuel was decreased by 68%.

Figure 7:
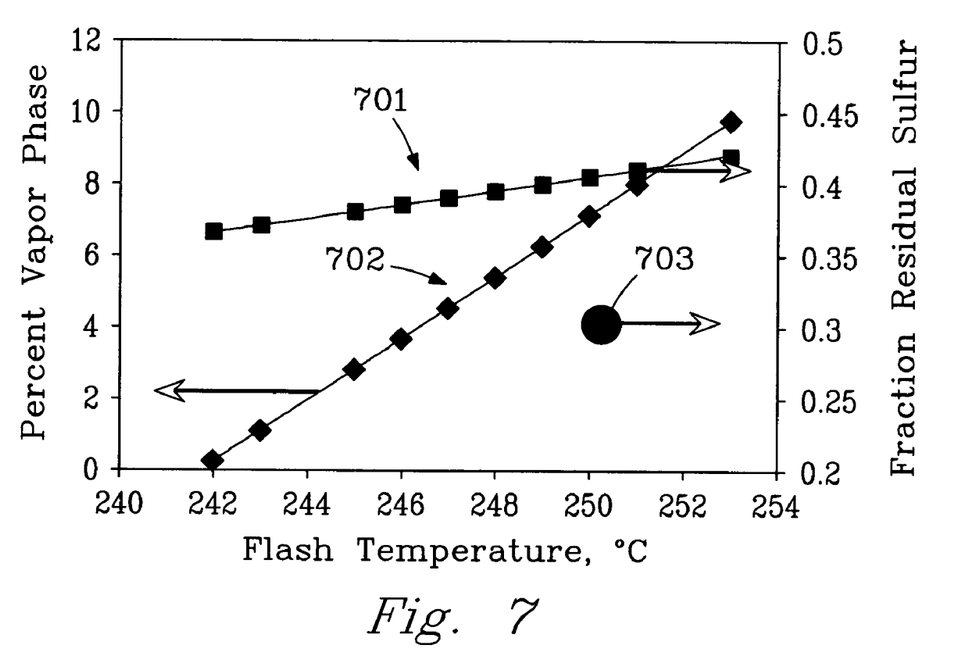
FIG. 7 Illustrates the flash distillation with 3000 ppm Dibenzothiophene inlet

FIG. 7, shows flash distillation results for 3000 ppm sulfur in the form of DBT, 4 methyl DBT and 4,6 methyl DBT with a concentration between about 50 and about 3073 ppmw. 701 represents the theoretical fraction of residual sulfur in the lower molecular weight component. 702 represents the theoretical fraction of the lower molecular weight component of the feedstock fuel. 703 represents the experimental results from the present invention. FIG. 7 further illustrates the present invention achieved 0.3 fraction of residual sulfur, indicating that the amount of sulfur in the fuel was decreased by 70%. It is also expected that regardless of how much sulfur is present in the fuel, similar results can be achieved.

The invention claimed is:

1. A process for producing hydrocarbon reagents in a logistical fuel after treatment system; said process comprising the steps of:
    a. Introducing a fuel containing hydrocarbons into a first step comprising a flash distillation process;
    b. Separating said fuel into a first component having a lower average molecular weight and a lower average sulfur concentration and a second component have a higher average molecular weight and a higher average sulfur concentration.
    c. Reforming said first component to produce a mixture of predominately synthesis gas; and
    d. Reacting said synthesis gas catalytically to produce a desired reagent; said reagent selected from the group consisting essentially of alcoholic products, ether products, olefinic products, ketone products, aldehyde products and combinations thereof.

2. The process in claim 1, wherein said reagents is selected from the group consisting of ethers, alcohols and combinations thereof.

3. The process in claim 2, wherein said ether is dimethyl ether.

4. The process in claim 2, wherein said alcohol is methanol.

5. The process in claim 2, wherein the reagents comprise a mixture of dimethyl ether to methanol in approximately a 4:1-8:1 ratio on a molar basis.

6. The process in claim 1, wherein the sulfur content of the first component is reduced to at least 20 ppb before reacting catalytically said synthesis gas to obtain a desired reagent.

7. The process in claim 1, wherein said reagents are selected from a group consisting of olefinic products, ketone products, aldehyde products and combinations thereof.

8. The process in claim 1, wherein said process is used to create a fuel supplement feedstock for a power source.

9. The process of claim 1, wherein said process is a part of a lean-NOx exhaust system and wherein said process is utilized to reduce the emissions emanating from said system.

10. The process in claim 1, wherein said reforming is selected from a group consisting of partial oxidation, autothermal, steam reforming, plasma reforming, super critical reforming, cracking, dry reforming and combinations thereof.

11. The process in claim 10, wherein said partial oxidation comprises the use of a precious group metal based catalyst.

* * * * *